United States Patent
Agano et al.

(10) Patent No.: US 7,677,800 B2
(45) Date of Patent: Mar. 16, 2010

(54) RADIOLOGICAL IMAGING APPARATUS, RADIOLOGICAL IMAGING METHOD, AND PROGRAM

(75) Inventors: Toshitaka Agano, Ashigarakami-gun (JP); Satoshi Arakawa, Ashigarakami-gun (JP); Atsushi Fukuda, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/045,383

(22) Filed: Mar. 10, 2008

(65) Prior Publication Data

US 2008/0232553 A1   Sep. 25, 2008

(30) Foreign Application Priority Data

Mar. 23, 2007   (JP) .............................. 2007-077608

(51) Int. Cl.
   *A61B 6/06* (2006.01)
(52) U.S. Cl. ...................................... 378/205
(58) Field of Classification Search ................. 378/205, 378/207
   See application file for complete search history.

(56) References Cited

U.S. PATENT DOCUMENTS

| | | | | |
|---|---|---|---|---|
| 6,379,042 | B1 * | 4/2002 | Polkus et al. ............... | 378/205 |
| 6,859,521 | B2 * | 2/2005 | Spahn ......................... | 378/205 |
| 2006/0280293 | A1 * | 12/2006 | Hardesty ..................... | 378/205 |
| 2008/0002808 | A1 * | 1/2008 | De Godzinsky .............. | 378/38 |
| 2008/0285723 | A1 * | 11/2008 | Lumma et al. ............... | 378/205 |

FOREIGN PATENT DOCUMENTS

| | | | |
|---|---|---|---|
| DE | 10302909 A1 | * | 8/2004 |
| JP | 60-5121 A | | 1/1985 |
| JP | 60-5124 U | | 1/1985 |
| JP | 200014664 A | | 7/1998 |
| JP | 2000-14664 A | | 1/2000 |

* cited by examiner

*Primary Examiner*—Chih-Cheng G Kao
(74) *Attorney, Agent, or Firm*—Sughrue Mion, PLLC (57) ABSTRACT

A radiological imaging apparatus that includes a radiation source, a radiation detection section that detects radiation that passes through a subject, a signal detection section that detects signals from a plurality of signal generating sections disposed on the radiation detection section, a signal comparison section that compares the signals detected by the signal detection section, a positional relationship judgment section that makes a judgment as to whether a positional relationship between the radiation detection section and the radiation source is a predetermined positional relationship, a position control section that controls a position of at least one of the radiation source and the radiation detection section to maintain the positional relationship, a position control holding section that holds and fixes the radiation source and the radiation detection section, and a notification section that provides notification in a case where the positional relationship is not the predetermined positional relationship during holding.

12 Claims, 6 Drawing Sheets

| A—C | B—D | CONTROL VALUE |
|---|---|---|
| STRENGTH DIFFERENCE $\alpha_1$ | STRENGTH DIFFERENCE $\beta_1$ | CONTROL VALUE CHANGE AMOUNT $\Delta \gamma_1$ |
| STRENGTH DIFFERENCE $\alpha_2$ | STRENGTH DIFFERENCE $\beta_2$ | CONTROL VALUE CHANGE AMOUNT $\Delta \gamma_2$ |
| ⋮ | ⋮ | ⋮ |

FIG. 5

| MAXIMUM | MINIMUM |
|---|---|
| CONTROL VALUE $\gamma_{max}$ | CONTROL VALUE $\gamma_{min}$ |

RADIOLOGICAL IMAGING APPARATUS, RADIOLOGICAL IMAGING METHOD, AND PROGRAM

CROSS REFERENCE TO RELATED APPLICATION

The present application claims priority from a Japanese Patent Application No. 2007-077608 filed on Mar. 23, 2007, the contents of which are incorporated herein by reference.

BACKGROUND

1. Technical Field

The present invention relates to a radiological imaging apparatus, a radiological imaging method, and a program and, more particularly, the present invention relates to a radiological imaging apparatus and a radiological imaging method that capture a radiological image and a program used by the radiological imaging apparatus.

2. Related Art

Technology by which a magnetic source that generates a magnetic field having a rotational target normal to a film is affixed to a back side of the film and the generated magnetic field is detected by three magnetic sensors disposed in a periphery of an illumination axis of an X-ray radiation cone is known as, for example, in Japanese Patent Application Publication No. sho60-5124 (Patent Document 1). Furthermore, technology by which a magnetic field from a magnetic transmitter disposed on a wall, table, or the like of the examination room is received by an X-ray generating section and an X-ray detecting section is known as, for example, in Japanese Patent Application Publication No. 2000-014664 (Patent Document 2).

Through the technology of Patent Document 1 and Patent Document 2 described above, a position of the film/X-ray detecting section can be specified to be aligned with a position of the radiation cone/X-ray generating section. For example, in a case where images are captured by a portable X-ray detector placed under a subject on a bed, the X-ray detector can easily be moved according to movement of a patient. Accordingly, after the film/X-ray detecting section is aligned with the radiation cone/X-ray generating section, there is a problem that misalignment arises in the positional relationship and the imaging fails where the subject moves immediately before the image is captured. On the other hand, where the position of the radiation cone/X-ray generating section is controlled to follow small movements of the subject, there is a danger that the position of the radiation cone/X-ray generating section cannot be stabilized.

SUMMARY

Therefore, it is an object of an aspect of the present invention to provide a radiological imaging apparatus, a radiological imaging method, and a program that are capable of overcoming the above drawbacks accompanying the related art. The above and other objects can be achieved by combinations described in the independent claims. The dependent claims define further advantageous and exemplary combinations of the present invention.

According to a first aspect related to the innovations herein, one exemplary apparatus may include a radiological imaging apparatus. The radiological imaging apparatus includes a radiation source that generates radiation irradiating a subject, a radiation detection section that detects radiation from the radiation source that passes through the subject, a signal detection section that detects signals from a plurality of signal generating sections disposed on the radiation detection section in a manner such that each signal generating section is in a different location, a signal comparison section that compares the signals from the plurality of signal generating sections detected by the signal detection section, a positional relationship judgment section that makes a judgment as to whether a positional relationship between the radiation detection section and the radiation source is a predetermined positional relationship based on a comparison result from the signal comparison section, a position control section that controls a position of at least one of the radiation source and the radiation detection section to maintain the positional relationship between the radiation source and the radiation detection section as the predetermined positional relationship based on a judgment result from the positional relationship judgment section, a position control holding section that holds the radiation source and the radiation detection section in the position set by the position control section after the position control section causes the positional relationship to be the prescribed positional relationship, and a notification section that provides notification in a case where the positional relationship judgment section makes a judgment that the positional relationship is not the prescribed positional relationship while the position control holding section is holding the radiation source and the radiation detection section in the position set by the position control section.

The signal detection section may detect wireless signals from the plurality of signal generating sections disposed on the radiation detection section and the signal comparison section may compare strengths of the wireless signals from the plurality of signal generating sections detected by the signal detection section.

The positional relationship judgment section may make a judgment as to whether the radiation detection section and the radiation source are facing each other based on a comparison result from the signal comparison section and the position control section may control at least one of the radiation source and the radiation detection section to cause the radiation source and the radiation detection section to face each other based on a judgment result from the positional relationship judgment section.

According to a second aspect related to the innovations herein, one exemplary method may include a radiological imaging method. The radiological imaging method includes detecting signals from a plurality of signal generating sections disposed in a manner such that each signal generating section is at a different location on a radiation detection section that detects radiation that passes through a subject from a radiation source that generates radiation that irradiates the subject, comparing the detected signals from the plurality of signal generating sections, making a judgment as to whether a positional relationship between the radiation detection section and the radiation source is a predetermined positional relationship based on a comparison result, controlling a position of at least one of the radiation source and the radiation detection section to maintain the positional relationship between the radiation source and the radiation detection section as the predetermined positional relationship based on a judgment result, holding the radiation source and the radiation detection section in the set position after the positional relationship is caused to be the prescribed positional relationship, and providing notification in a case where the judgment is made that the positional relationship is not the prescribed positional relationship while the radiation source and the radiation detection section are being held in the set position.

According to a third aspect related to the innovations herein, one exemplary program may include a program used by a radiological imaging apparatus. The program causes the radiological imaging apparatus to function as a radiation source that generates radiation irradiating a subject, a radiation detection section that detects radiation from the radiation source that passes through the subject, a signal detection section that detects signals from a plurality of signal generating sections disposed on the radiation detection section in a manner such that each signal generating section is in a different location, a signal comparison section that compares the signals from the plurality of signal generating sections detected by the signal detection section, a positional relationship judgment section that makes a judgment as to whether a positional relationship between the radiation detection section and the radiation source is a predetermined positional relationship based on a comparison result from the signal comparison section, a position control section that controls a position of at least one of the radiation source and the radiation detection section to maintain the positional relationship between the radiation source and the radiation detection section as the predetermined positional relationship based on a judgment result from the positional relationship judgment section, a position control holding section that holds the radiation source and the radiation detection section in the position set by the position control section after the position control section causes the positional relationship to be the prescribed positional relationship, and a notification section that provides notification in a case where the positional relationship judgment section makes a judgment that the positional relationship is not the prescribed positional relationship while the position control holding section is holding the radiation source and the radiation detection section in the position set by the position control section.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

Through the present invention, a radiological imaging apparatus is provided that can capture a radiation image in a condition in which the radiation source and the radiation detection section are in the appropriate positional relationship.

DESCRIPTION OF EXEMPLARY EMBODIMENTS

Hereinafter, an embodiment of the present invention will be described. The embodiment does not limit the invention according to the claims, and all the combinations of the features described in the embodiment are not necessarily essential to means provided by aspects of the invention.

Figure 1:
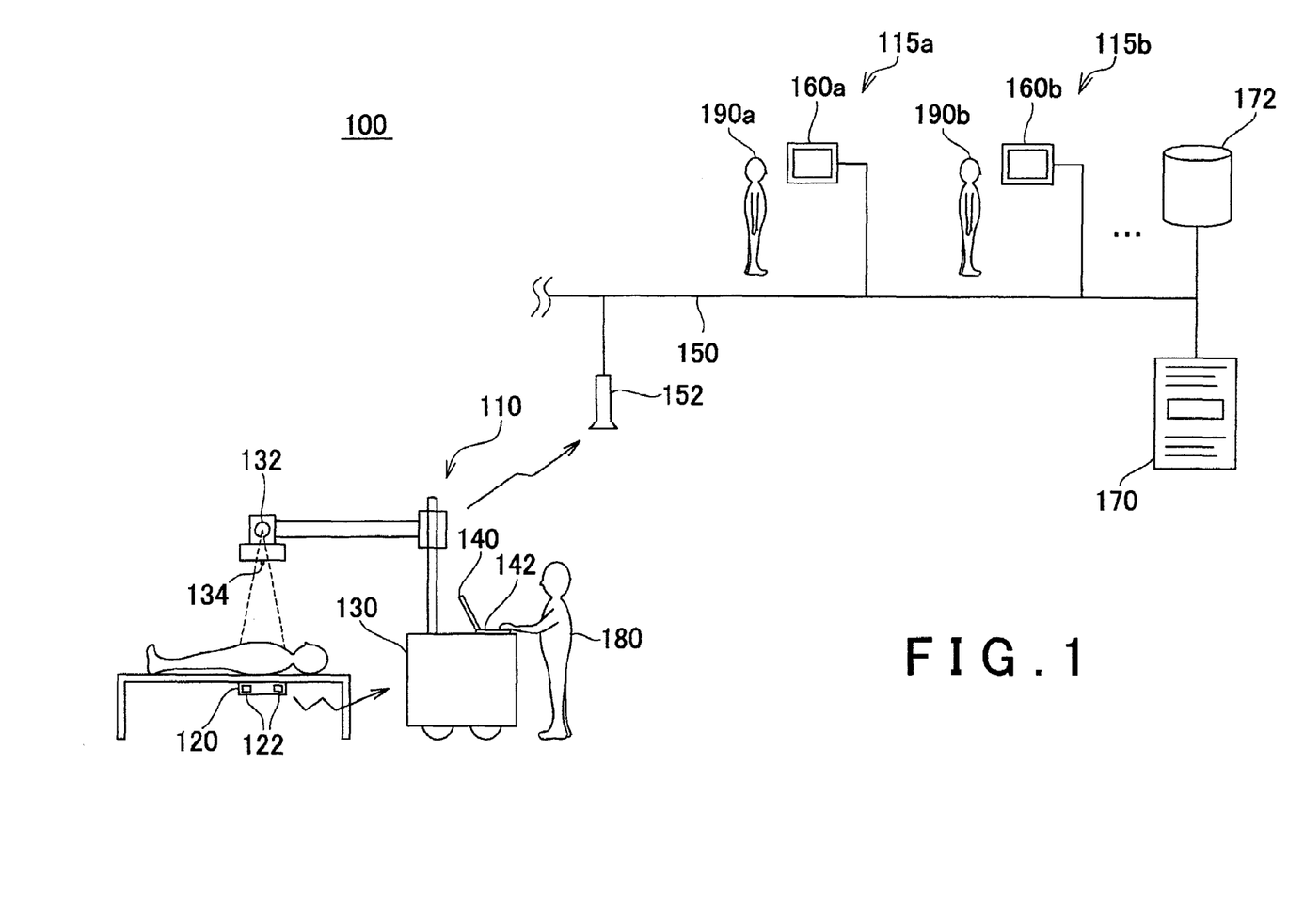
FIG. 1 shows an exemplary environment in which a radiological imaging system 100 according to the present embodiment is used.

FIG. 1 shows an exemplary environment in which a radiological imaging system 100 according to the present embodiment is used. The radiological imaging system 100 is provided with a radiological imaging apparatus 110, a communication path 150, a wireless communication apparatus 152, diagnostic apparatuses 115a, 115b (referred to hereinafter collectively as the diagnostic apparatuses 115), a server 170, and a database 172. The radiological imaging apparatus 110 includes an X-ray detector 120, a control apparatus 130, and a plurality of wireless transmitters 122 disposed at different locations of the X-ray detector 120. Each wireless transmitter 122 of the plurality of wireless transmitters 122 is disposed on a detection surface with which the X-ray detector 120 detects the X-rays at a location separated a prescribed distance from a center of the detection surface. The control apparatus 130 includes a monitor 140, an input apparatus 142, an X-ray source 132, and a wireless detector 134. Furthermore, the diagnostic apparatus 115a includes a monitor 160a and the diagnostic apparatus 115b includes a monitor 160b.

The radiological imaging apparatus 110 captures an X-ray image of a subject according to an operation of a radiological technician 180. The radiological imaging apparatus 110 may be a movable radiological imaging apparatus and the radiological imaging apparatus 110 can capture an X-ray image at an examination room in which the subject is present or at a home of the subject based on the operation of the radiological technician 180. Before capturing an image of the subject, the radiological imaging apparatus 110 receives an order for imaging of the subject from the server 170 via the communication path 150 and the wireless communication apparatus 152 in a proximity of the radiological imaging apparatus 110. The monitor 140 then displays the ID, full name, age, gender, weight, imaging region, and imaging direction of the subject, all of which are included in the imaging order.

The radiological technician 180 then determines imaging conditions based on the age, gender, weight, and imaging region displayed on the monitor 140 and inputs the imaging conditions into the input apparatus 142. The imaging conditions include tube current, tube voltage, diaphragm of the X-ray source 132, and radiation time. The radiological imaging apparatus 110 may also receive the imaging conditions from the server 170.

The wireless detector 134 is disposed in a proximity of the X-ray source 132, and the control apparatus 130 fixes a position of the X-ray source 132 after positioning the X-ray source 132 in a manner such that strengths of the wireless signals transmitted from the plurality of wireless transmitters 122 and detected by the wireless detector 134 are uniform. The control apparatus 130 constantly detects the strength of the wireless signal transmitted from the wireless transmitters 122 even after the position of the X-ray source 132 is fixed. The control apparatus 130 then makes a judgment based on the strength of the wireless signals as to whether a misalignment arises in a positional relationship between the X-ray detector 120 and the X-ray source 132 after the position of the X-ray source 132 is fixed. Then, where a judgment is made that a misalignment has arisen, the control apparatus 130 prohibits generation of X-rays form the X-ray source 132 and displays on the monitor 140 notification that a misalignment has arisen.

In a case where a misalignment does not arise, the control apparatus 130 causes the X-ray source 132 to radiate X-rays. The X-ray detector 120 generates an X-ray image from a signal achieved according to an amount of X-rays that pass through the subject and sends the X-ray image to the server 170 via the control apparatus 130. The server 170 records the received X-ray image in the database 172. The diagnostic apparatus 115 acquires the X-ray image from the database 172 and displays the X-ray image on the monitor 160 according to an operation by physicians 190a, 190b (referred to hereinafter collectively as the physicians 190). Only one radiological imaging apparatus 110 is shown here, but the radiological imaging system 100 may be provided with a plurality of radiological imaging apparatuses 110. Furthermore, control of a series of communications and recording of image data in the above description may be executed according to a DICOM code. The X-ray detector 120 may include an imaging plate that uses a photostimulable phosphor and an X-ray film that is sensitive to X-rays (including an intensifying screen). Furthermore, the X-ray detector 120 may be a solid X-ray detector such as an FPD.

Figure 2:
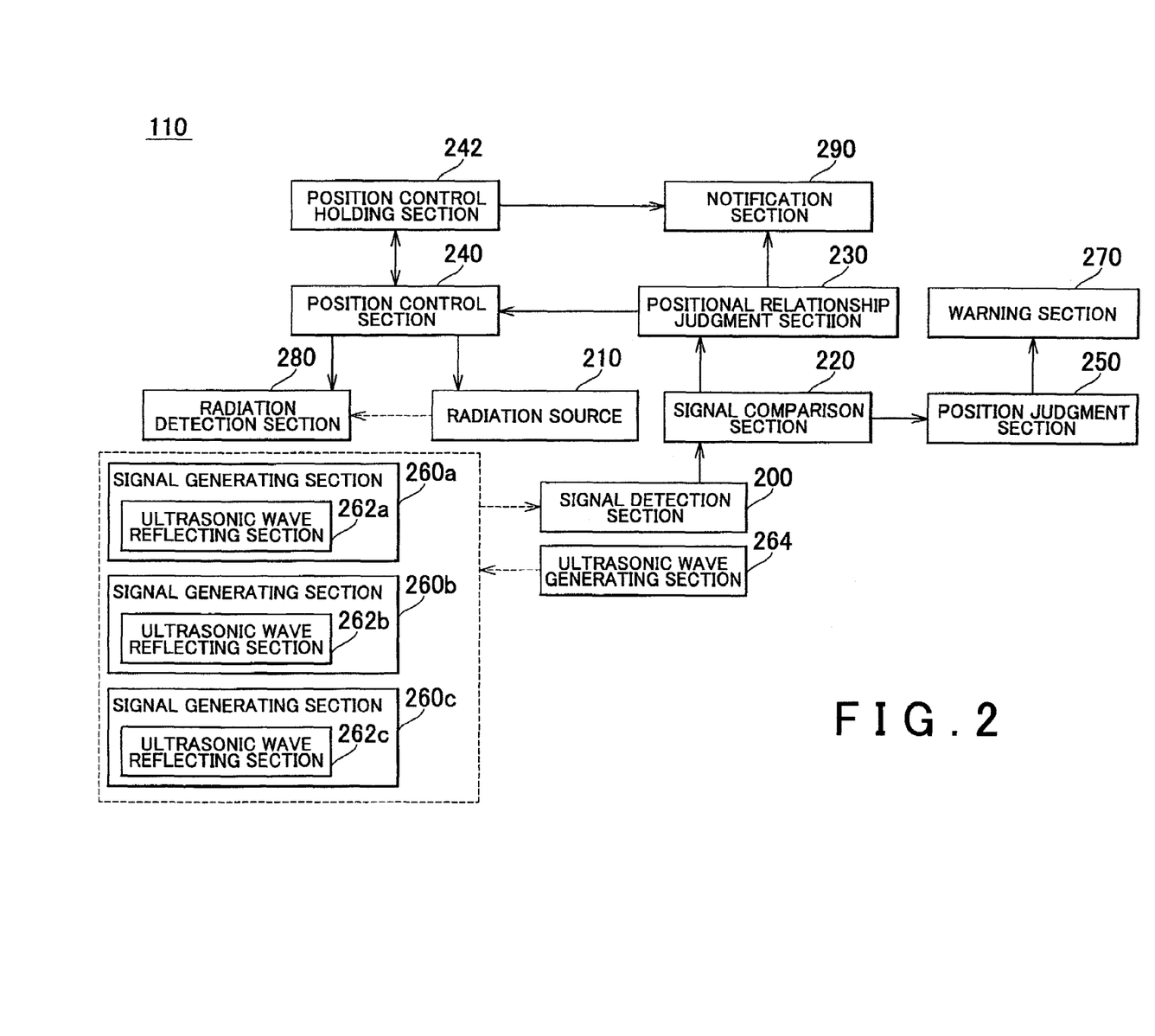
FIG. 2 shows an exemplary block configuration of the radiological imaging apparatus 110.

FIG. 2 shows an exemplary block configuration of the radiological imaging apparatus 110. The radiological imaging apparatus 110 is provided with a signal detection section 200, a radiation detection section 280, a signal comparison section 220, a positional relationship judgment section 230, a position control section 240, a position control holding section 242, a position judgment section 250, a plurality of signal generating sections 260a~c (referred to hereinafter collectively as the signal generating sections 260), a warning section 270, a radiation source 210, and a notification section 290.

The signal generating sections 260a~c may include ultrasonic wave reflecting sections 262a~c (referred to hereinafter collectively as the ultrasonic wave reflecting sections 262) respectively. In a case where the signal generating sections 260 include the ultrasonic wave reflecting sections 262, the radiological imaging apparatus 110 may include an ultrasonic wave generating section 264. The X-ray source 132 is one example of the radiation source 210 and the X-ray detector 120 is one example of the radiation detection section 280. Furthermore, the wireless transmitter 122 is one example of the signal generating section 260 and the wireless detector 134 is one example of the signal detection section 200.

The radiation source 210 generates the radiation that irradiates the subject. The radiation detection section 280 detects the radiation from the radiation source 210 that passes through the subject. The signal detection section 200 detects signals from the plurality of signal generating sections 260 disposed at different locations on the radiation detection section 280. The signal comparison section 220 compares the signals from the plurality of signal generating sections 260 detected by the signal detection section 200. Specifically, the signal detection section 200 detects the wireless signals from the plurality of signal generating sections 260 disposed on the radiation detection section 280. The signal comparison section 220 then compares phases of the wireless signals from the plurality of signal generating sections 260 detected by the signal detection section 200. As another possibility, the signal comparison section 220 may compare signal strengths of the wireless signals from the plurality of signal generating sections 260 detected by the signal detection section 200.

The positional relationship judgment section 230 then makes a judgment as to whether a positional relationship between the radiation detection section 280 and the radiation source 210 is a predetermined positional relationship based on a comparison result from the signal comparison section 220. The position control section 240 then controls the position of at least one of the radiation source 210 and the radiation detection section 280 to maintain the positional relationship between the radiation source 210 and the radiation detection section 280 as the predetermined positional relationship based on a judgment result from the positional relationship judgment section 230. For example, the positional relationship judgment section 230 makes a judgment as to whether the radiation detection section 280 and the radiation source 210 are facing each other based on the comparison result from the signal comparison section 220. The position control section 240 then controls the position of at least one of the radiation source 210 and the radiation detection section 280 to cause the radiation source 210 and the radiation detection section 280 to face each other based on a judgment result from the positional relationship judgment section 230.

After the position control section 240 sets the aforementioned positional relationship to be the predetermined positional relationship, the position control holding section 242 holds the radiation source 210 and the radiation detection section 280 in the position set by the position control section 240. Then, the notification section 290 notifies a user in a case where the positional relationship judgment section 230 makes a judgment that the positional relationship is not the predetermined positional relationship while the position control holding section 242 holds the radiation source 210 and the radiation detection section 280 in the position set by the position control section 240.

The position judgment section 250 makes a judgment as to whether the radiation source 210 and the radiation detection section 280 can be kept in the predetermined positional relationship based on the comparison result from the signal comparison section 220 and a range in which the radiation source 210 and the radiation detection section 280 can move. The warning section 270 then warns the user in a case where the position judgment section 250 makes a judgment that the radiation source 210 and the radiation detection section 280 cannot be kept in the predetermined positional relationship.

The signal detection section 200 detects signals from three or more of the signal generating sections 260 disposed at different locations on the radiation detection section 280. The positional relationship judgment section 230 makes a judgment as to whether the positional relationship in three-dimensional space between the radiation detection section 280 and the radiation source 210 is the predetermined positional relationship based on the comparison result from the signal comparison section 220.

The signal detection section 200 may be disposed in a proximity of the radiation source 210. Furthermore, the signal detection section 200 may be disposed on an illumination axis on which radiation is radiated between the radiation source 210 and the radiation detection section 280. Yet further, the plurality of signal generating sections 260 may be disposed at opposite corners of the radiation detection section 280 shaped as a rectangle. More specifically, the plurality of signal generating sections 260 may be disposed on at least three corners of the rectangular radiation detection section 280.

Furthermore, the ultrasonic wave generating section 264 sends ultrasonic waves to the radiation detection section 280. The signal detection section 200 may then detect the ultrasonic waves reflected by the ultrasonic wave reflecting sections 262 contained in each signal generating section 260 in the plurality of signal generating sections 260. The signal comparison section 220 may then compare the times from when the ultrasonic waves are sent by the ultrasonic wave generating section 264 to when the signal detection section 200 detects the ultrasonic waves from the ultrasonic wave reflecting sections 262.

The radiation in the present embodiment includes particle beams such as alpha-rays or electromagnetic radiation such as gamma-rays in addition to X-rays.

Figure 3:
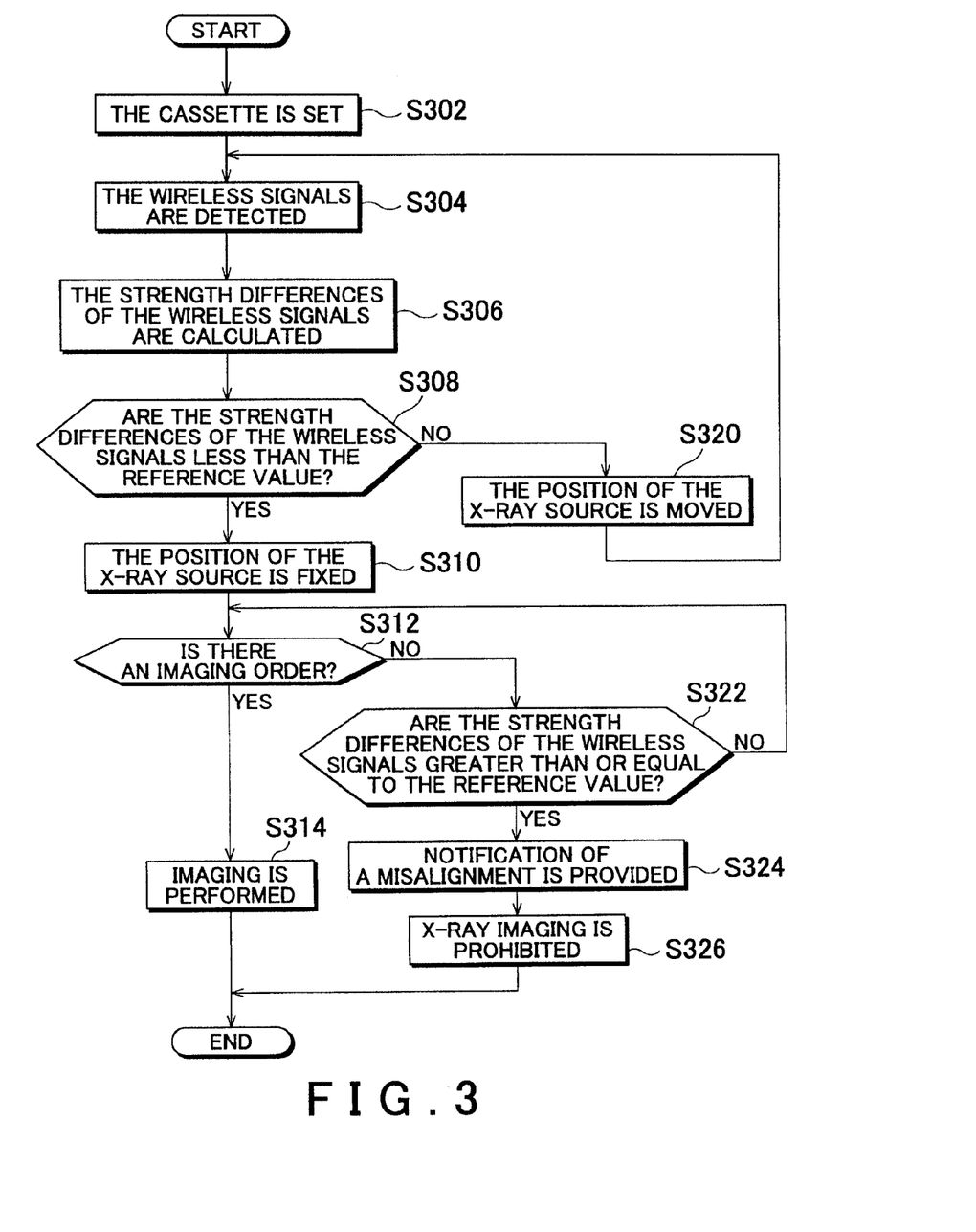
FIG. 3 shows an exemplary flow of imaging by the radiological imaging apparatus 110.

FIG. 3 shows an exemplary flow of imaging by the radiological imaging apparatus 110. Where a cassette, which is one example of the radiation detection section 280, is set by the radiological technician 180 (S302), the wireless detector 134 detects the wireless signals from each wireless transmitter 122 in the plurality of wireless transmitters 122 (S304). The signal comparison section 220 then calculates strength differences of the wireless signals detected by the wireless detector 134 (S306).

The positional relationship judgment section 230 then makes a judgment as to whether the strength differences of the wireless signals calculated at S306 are smaller than a predetermined reference value (S308). In a case where the strength differences of the wireless signals are less than the predetermined reference value, the positional relationship judgment section 230 makes a judgment that the X-ray detector 120 and the X-ray source 132 are facing each other.

In a case where the positional relationship judgment section 230 makes a judgment that the strength differences of the wireless signals are greater than or equal to the predetermined reference value, the position control section 240 moves the position of the X-ray source 132 according to the strength differences of the wireless signals (S320) and the process returns to S304. At this time, in a case where the X-ray source 132 cannot be moved to a position that causes the strength differences of the wireless signals to be less than the reference value, the warning section 270 notifies the radiological technician 180 by displaying on the monitor 140 notification that the position of the X-ray source 132 cannot be moved.

In a case where the positional relationship judgment section 230 makes a judgment that the strength differences of the wireless signals are less than the reference value, the position control holding section 242 holds the position of the X-ray source 132 set by the position control section 240, so that the position of the X-ray source 132 is fixed (S310).

The control apparatus 130 then makes a judgment as to whether capturing of the X-ray image is ordered from the radiological technician 180 via the input apparatus 142 (S312). In a case where capturing of the X-ray image is ordered, the control apparatus 130 causes the X-ray source 132 to generate X-rays and causes the X-ray detector 120 to capture the X-ray image obtained from the X-rays that pass through the subject (S314), after which the process is finished.

In a case where capturing of the X-ray image is not ordered, in the same manner as S304 and S306, the strength differences of the wireless signals are calculated and a judgment is made as to whether the strength differences of the wireless signals are greater than or equal to the reference value (S322). In a case where the strength differences of the wireless signals are less than the reference value, the process moves to step S312 (S312). In a case where the strength differences of the wireless signals are greater than or equal to the reference value, the notification section 290 notifies the radiological technician 180 by displaying in the monitor 140 notification that a misalignment has arisen in the positional relationship between the X-ray detector 120 and the X-ray source 132 (S324). The control apparatus 130 then prohibits the X-ray source 132 from generating X-rays (S326), after which the process is finished.

Figure 4:
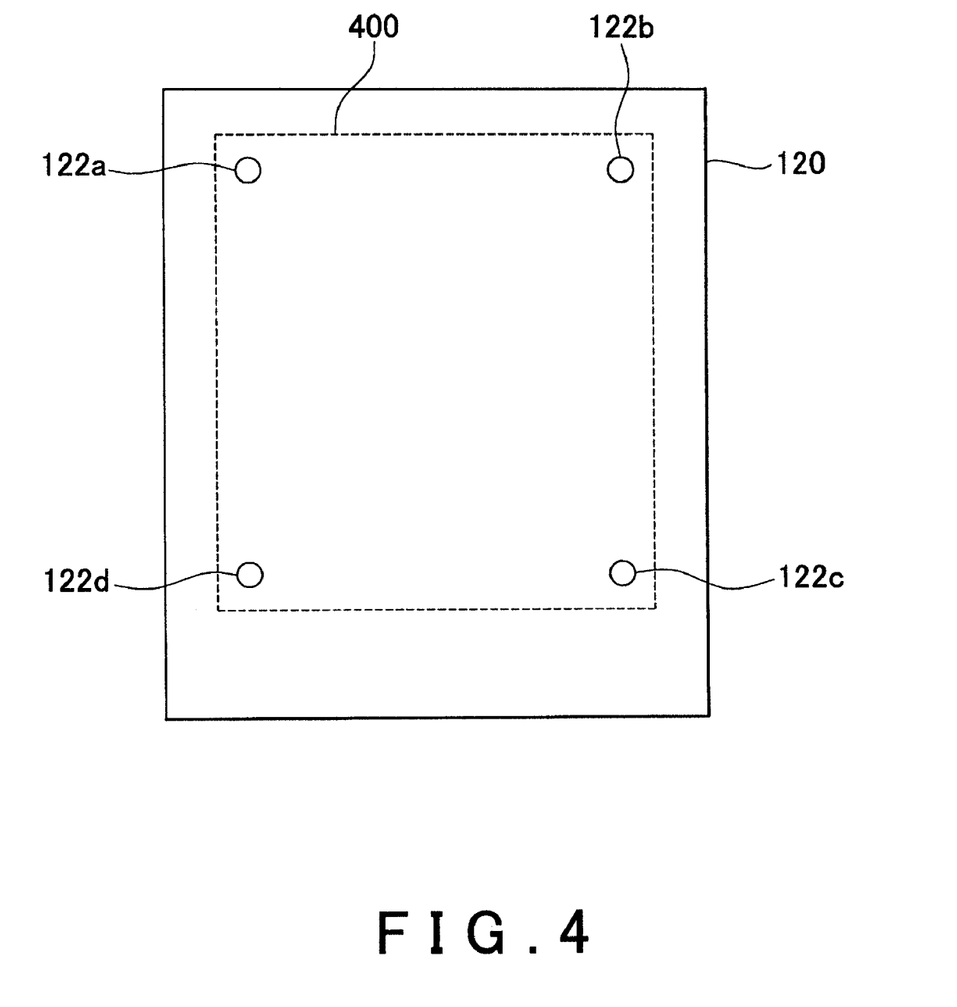
FIG. 4 shows an exemplary arrangement of wireless transmitters 122.

FIG. 4 shows an exemplary arrangement of the wireless transmitters 122a-d in the X-ray detector 120. The wireless transmitters 122 in the present embodiment refer to the wireless transmitters 122a-d collectively. The wireless transmitters 122 are disposed at four corners of a detection surface 400 with which the X-ray detector 120 detects the X-rays. The wireless transmitters 122 include signals that distinguish one from another and send wireless signals such as electrical waves. The wireless transmitters 122 may generate wireless signals having generally the same strength.

The X-ray detector 120 may include a plurality of ultrasonic wave reflecting sections 262 at the four corners of the detection surface 400 instead of the wireless transmitters 122. In such a case, the signal detection section 200 detects the ultrasonic waves that are generated from the ultrasonic wave generating section 264 and reflected by the ultrasonic wave reflecting sections 262. The ultrasonic wave reflecting sections 262 may each have a different size, shape, and hardness such that the signal detection section 200 can distinguish the position of each ultrasonic wave reflecting section 262.

Figure 5:
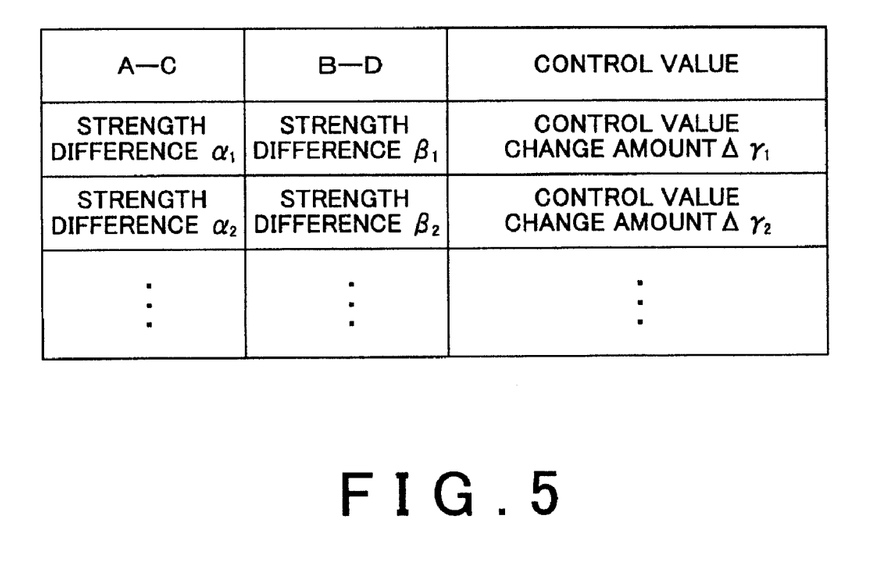
FIG. 5 shows a table of exemplary data stored by a position control section 240.

FIG. 5 shows a table of exemplary data stored by the position control section 240. The position control section 240 stores an amount of change in a control value for the change in position of the X-ray source 132 by the position control section 240 in association with the strength differences of the wireless signals transmitted from the plurality of wireless transmitters 122 and detected by the signal detection section 200. The control value may be, for example, a current value, a voltage value, or the like that is supplied to a driving apparatus that drives the X-ray source 132 to change the position of the X-ray source 132 or may be a length of time that the driving by the driving apparatus is controlled.

Here, where the strengths of the wireless signals transmitted by the wireless transmitter 122a, the wireless transmitter 122b, the wireless transmitter 122c, and the wireless transmitter 122d and detected by the signal detection section 200 are set to A, B, C, and D, respectively, the position control section 240 stores each amount of change in the control values $\Delta\gamma$ in association with a strength difference A-C and a strength difference B-D.

Specifically, the position control section 240 stores an amount of change in the control value $\Delta\gamma1$ in association with a case where $\alpha1$ and $\beta1$ are A-C and B-D, respectively. Accordingly, in a case where the strength difference A-C is $\alpha1$ and the strength difference B-D is $\beta1$, the position control section 240 changes the control value by only $\Delta\gamma1$. The position control section 240 may store the amount of change in the control values $\Delta\gamma$ in association with a strength ratio instead of the strength difference. As another example, the position control section 240 may store the amount of change in the control values $\Delta\gamma$ in association with strength differences obtained from all combinations of strength differences of each of the wireless signals transmitted from each wireless transmitter 122 in the plurality of wireless transmitters 122 and detected by the signal detection section 200 (for example, A-B, A-C, A-D, B-C, B-D, C-D).

In FIG. 5, a case is described where the amount of change in the control values is stored in association with the strength differences of the wireless signals, but it goes without saying that the position control section 240 may store the amount of change in the control values $\Delta\gamma$ in association with a range of the strength differences between the wireless signals. Furthermore, the position control section 240 may store the amount of change in the control values $\Delta\gamma$ in association with strength differences of the ultrasonic waves. In such a case, the position control section 240 may change the control value by only the amount of change in the control value Δγ stored in association with the strength differences of the ultrasonic waves detected by the signal detection section 200.

Figure 6:
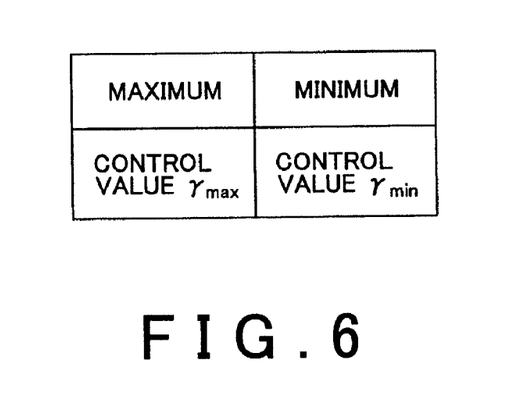
FIG. 6 shows a table of exemplary data stored by a position judgment section 250.

FIG. 6 shows a table of exemplary data stored by the position judgment section 250. The position judgment section 250 stores a maximum value γmax of the control value and a minimum value γmin of the control value. The position judgment section 250 can reference the data stored by the position control section 240 explained in relation to FIG. 5. At a time when the control value is changed from the current control value by the amount of change in the control value Δγ stored by the position control section 240 in association with the strength differences of the wireless signals calculated by the signal comparison section 220, the position judgment section 250 makes a judgment that the X-ray source 132 and the X-ray detector 120 can be held in the predetermined positional relationship in a case where the control value is greater than or equal to γmin and less than or equal to γmax.

Then, in a case where γ+Δγ, which is the control value changed from the current control value γ by the amount of change Δγ, falls below γmin or rises above γmax, a judgment is made that the X-ray source 132 and the X-ray detector 120 cannot be held in the predetermined positional relationship. At this time, the warning section 270 warns that the X-ray source 132 cannot be caused to face the X-ray detector 120. In such a case, the control apparatus 130 may prohibit the X-ray source 132 from generating X-rays.

In the description above, an example is described of a case where the position of the X-ray source 132 is controlled, but the control apparatus 130 can also cause the X-rays generated by the X-ray source 132 to irradiate the detection surface 400 of the X-ray detector 120 at a generally right angle through the same control as described above. For example, the signal detection section 200 is disposed in a proximity of the focal point of the X-ray source 132 and the position control section 240 controls the position of the X-ray source 132 based on a comparison result of the wireless signals from the signal generating section 260 as described above.

Furthermore, the signal detection section 200 detects a signal generated by the signal generating sections 260 at a position different from the position in a proximity of the aforementioned focal point on an illumination axis of the X-rays radiated from the X-ray source 132. Through the same method as described above, the position control section 240 causes the X-ray source 132 to rotate, for example, in a manner to cause the strength difference of the signals to be less than the reference value based on the comparison result of the signals from the signal generating section 260. At this time, the position control section 240 causes the X-ray source 132 to rotate with the focal point of the X-ray source 132 as the rotational axis. Through the control described above, the control apparatus 130 can cause the X-rays generated by the X-ray source 132 to irradiate the detection surface 400 of the X-ray detector 120 at a generally right angle. In a case where the radiation direction of the X-rays is controlled in the manner described above, the signal detection section 200 may be disposed at a position in a proximity of the focal point of the X-ray source 132 and at more than one position different from the position in the proximity of the focal point on the illumination axis of the X-rays.

Furthermore, the embodiment described above describes a configuration in which the wireless transmitters 122 are disposed on the X-ray detector 120 and the signals from the wireless transmitters 122 are detected by the control apparatus 130. In other configurations, the wireless transmitters 122 may be disposed on the control apparatus 130 and the signal detection section 200 may be disposed on the X-ray detector 120. In other words, the plurality of signal detection sections 200 is disposed such that the detection sections are at locations differing from one another on the radiation detection section 280 and detects the signals from the signal generating sections 260. The signal comparison section 220 then compares the signals from the signal generating sections 260 detected by the plurality of signal detection sections 200. The positional relationship judgment section 230 then makes a judgment as to whether the positional relationship between the radiation detection section 280 and the radiation source 210 is the predetermined positional relationship based on the comparison result from the signal comparison section 220. The position control section 240 then controls the position of at least one of the radiation source 210 and the radiation detection section 280 to maintain the positional relationship between the radiation source 210 and the radiation detection section 280 as the predetermined positional relationship based on the judgment result from the positional relationship judgment section 230.

Figure 7:
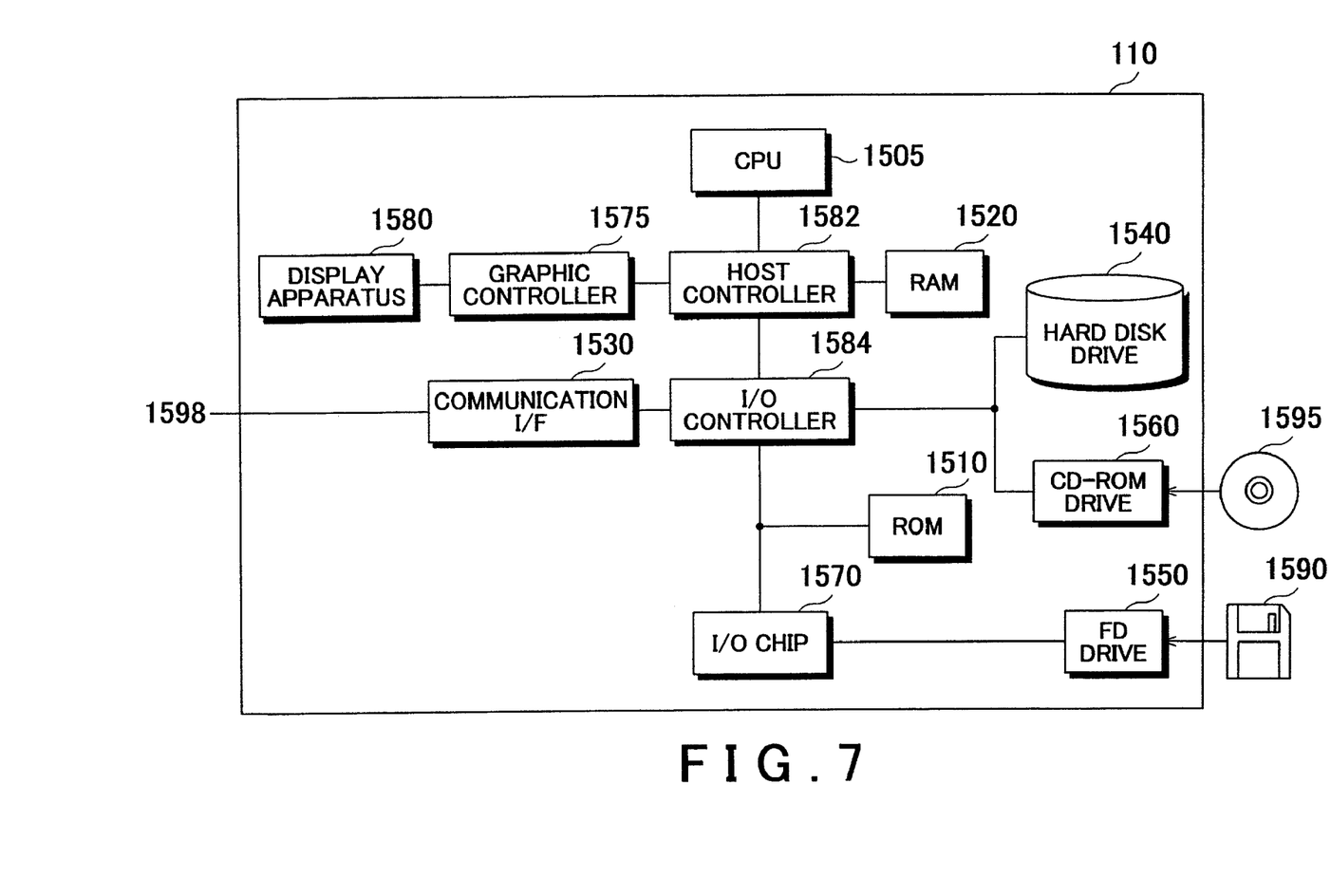
FIG. 7 shows an exemplary hardware configuration of the radiological imaging apparatus 110.

FIG. 7 shows an exemplary hardware configuration of the radiological imaging apparatus 110. The radiological imaging apparatus 110 according to the present embodiment is provided with a CPU peripheral section that includes a CPU 1505, a RAM 1520, a graphic controller 1575, and a display apparatus 1580 connected to each other by a host controller 1582; an input/output section that includes a communication interface 1530, a hard disk drive 1540, and a CD-ROM drive 1560, all of which are connected to the host controller 1582 by an input/output controller 1584; and a legacy input/output section that includes a ROM 1510, a flexible disk drive 1550, and an input/output chip 1570, all of which are connected to the input/output controller 1584.

The host controller 1582 is connected to the RAM 1520 and is also connected to the CPU 1505 and graphic controller 1575 accessing the RAM 1520 at a high transfer rate. The CPU 1505 operates to control each section based on programs stored in the ROM 1510 and the RAM 1520. The graphic controller 1575 acquires image data generated by the CPU 1505 or the like on a frame buffer disposed inside the RAM 1520 and displays the image data in the display apparatus 1580. In addition, the graphic controller 1575 may internally include the frame buffer storing the image data generated by the CPU 1505 or the like.

The input/output controller 1584 connects the hard disk drive 1540, the communication interface 1530 serving as a relatively high speed input/output apparatus, and the CD-ROM drive 1560 to the host controller 1582. The hard disk drive 1540 stores the programs and data used by the CPU 1505. The communication interface 1530 is connected to a network communication apparatus 1598 and receives the programs or the data. The CD-ROM drive 1560 reads the programs and data from a CD-ROM 1595 and provides the read information to the hard disk drive 1540 and the communication interface 1530 via the RAM 1520.

Furthermore, the input/output controller 1584 is connected to the ROM 1510, and is also connected to the flexible disk drive 1550 and the input/output chip 1570 serving as a relatively high speed input/output apparatus. The ROM 1510 stores a boot program performed when the radiological imaging apparatus 110 starts up, a program relying on the hardware of the radiological imaging apparatus 110, and the like. The flexible disk drive 1550 reads programs or data from a flexible disk 1590 and supplies the read information to the hard disk drive 1540 and the communication interface 1530 via the RAM 1520. The input/output chip 1570 connects the flexible disk drive 1550 to each of the input/output apparatuses via, for example, a parallel port, a serial port, a keyboard port, a mouse port, or the like.

The programs performed by the CPU 1505 are stored on a recording medium such as the flexible disk 1590, the CD-ROM 1595, or an IC card and are provided by the user. The programs stored on the recording medium may be compressed or uncompressed. The programs are installed on the hard disk drive 1540 from the recording medium, are read by the RAM 1520, and are performed by the CPU 1505.

The programs performed by the CPU 1505 cause the radiological imaging apparatus 110 to function as the signal detection section 200, the radiation detection section 280, the signal comparison section 220, the positional relationship judgment section 230, the position control section 240, the position control holding section 242, the position judgment section 250, the signal generating section 260, the warning section 270, the radiation source 210, and the notification section 290 described in FIGS. 1 to 7.

The programs shown above may be stored in an external storage medium. In addition to the flexible disk 1590 and the CD-ROM 1595, an optical recording medium such as a DVD or PD, a magnetooptical medium such as an MD, a tape medium, a semiconductor memory such as an IC card, or the like can be used as the recording medium. Furthermore, a storage apparatus such as a hard disk or a RAM disposed in a server system connected to the Internet or a specialized communication network may be used as the storage medium and the programs may be provided to the radiological imaging apparatus 110 via the network.

While the embodiment of the present invention has been described, the technical scope of the invention is not limited to the above described embodiment. It is apparent to persons skilled in the art that various alterations and improvements can be added to the above-described embodiment. It is also apparent from the scope of the claims that the embodiments added with such alterations or improvements can be included in the technical scope of the invention.

What is claimed is:

1. A radiological imaging apparatus, comprising:
    a radiation source that generates radiation irradiating a subject;
    a radiation detection section that detects radiation from the radiation source that passes through the subject;
    a signal detection section that detects signals from a plurality of signal generating sections disposed on the radiation detection section in a manner such that each signal generating section is in a different location;
    a signal comparison section that compares the signals from the plurality of signal generating sections detected by the signal detection section;
    a positional relationship judgment section that makes a judgment as to whether a positional relationship between the radiation detection section and the radiation source is a predetermined positional relationship based on a comparison result from the signal comparison section;
    a position control section that controls a position of at least one of the radiation source and the radiation detection section to maintain the positional relationship between the radiation source and the radiation detection section as the predetermined positional relationship based on a judgment result from the positional relationship judgment section;
    a position control holding section that holds the radiation source and the radiation detection section in the position set by the position control section and fixes the positional relationship between the radiation detection section and the radiation source after the position control section causes the positional relationship to be the predetermined positional relationship;
    a notification section that provides notification in a case where the positional relationship judgment section makes a judgment that the positional relationship is not the predetermined positional relationship while the position control holding section is holding the radiation source and the radiation detection section in the position set by the position control section;
    a position judgment section that makes a judgment as to whether the radiation source and the radiation detection section can be held in the predetermined positional relationship based on a comparison result from the signal comparison section and a range in which the radiation source and the radiation detection section can move; and
    a warning section that warns a user in a case where the position judgment section makes a judgment that the radiation source and the radiation detection section cannot be held in the predetermined positional relationship.

2. The radiological imaging apparatus according to claim 1, wherein: the signal detection section detects wireless signals from the plurality of signal generating sections disposed on the radiation detection section; and
    the signal comparison section compares phases of the wireless signals from the plurality of signal generating sections detected by the signal detection section.

3. The radiological imaging apparatus according to claim 1, wherein: the signal detection section detects wireless signals from the plurality of signal generating sections disposed on the radiation detection section; and
    the signal comparison section compares strengths of the wireless signals from the plurality of signal generating sections detected by the signal detection section.

4. The radiological imaging apparatus according to claim 1, wherein:
    the positional relationship judgment section makes a judgment as to whether the radiation detection section and the radiation source are facing each other based on a comparison result from the signal comparison section; and
    the position control section controls a position of at least one of the radiation source and the radiation detection section to cause the radiation source and the radiation detection section to face each other based on a judgment result from the positional relationship judgment section.

5. The radiological imaging apparatus according to claim 1, wherein:
    the signal detection section detects signals from three or more signal generating sections disposed on the radiation detection section in a manner such that each signal generating section is in a different location; and
    the positional relationship judgment section makes a judgment as to whether a positional relationship in three-dimensional space between the radiation detection section and the radiation source is a predetermined positional relationship based on a comparison result from the signal comparison section.

6. The radiological imaging apparatus according to claim 1, wherein the signal detection section is disposed in a proximity of the radiation source.

7. The radiological imaging apparatus according to claim 1, wherein the signal detection section is disposed in a proximity of a focal point of the radiation source.

8. The radiological imaging apparatus according to claim 1, wherein the plurality of signal generating sections are located at opposite corners of the radiation detection section having a rectangular shape.

9. The radiological imaging apparatus according to claim 1, wherein the plurality of signal generating sections are located at a minimum of three corners of the radiation detection section having a rectangular shape.

10. The radiological imaging apparatus according to claim 1, further comprising an ultrasonic wave generating section that sends out ultrasonic waves to the radiation detection section, wherein:
   each signal generating section in the plurality of signal generating sections includes an ultrasonic wave reflecting section that reflects the ultrasonic waves sent out from the ultrasonic wave generating section;
   the signal detection section detects the ultrasonic waves reflected by the ultrasonic wave reflecting sections included in each signal generating section in the plurality of signal generating sections; and
   the signal comparison section compares times from when the ultrasonic wave generating section sends out the ultrasonic waves to when the signal detection section detects the ultrasonic waves from the ultrasonic wave reflecting sections.

11. A radiological imaging method, comprising:
   detecting signals from a plurality of signal generating sections disposed in a manner such that each signal generating section is at a different location on a radiation detection section that detects radiation that passes through a subject from a radiation source that generates radiation that irradiates the subject;
   comparing the detected signals from the plurality of signal generating sections;
   making a judgment as to whether a positional relationship between the radiation detection section and the radiation source is a predetermined positional relationship based on a comparison result;
   controlling a position of at least one of the radiation source and the radiation detection section to maintain the positional relationship between the radiation source and the radiation detection section as the predetermined positional relationship based on a judgment result;
   holding the radiation source and the radiation detection section in the set position and fixing the positional relationship between the radiation detection section and the radiation source after the positional relationship is caused to be the predetermined positional relationship;
   providing notification in a case where a judgment is made that the positional relationship is not the predetermined positional relationship while the radiation source and the radiation detection section are being held in the set position;
   making a judgment as to whether the radiation source and the radiation detection section can be held in the predetermined positional relationship based on a comparison result and a range in which the radiation source and the radiation detection section can move; and
   warning a user in a case where a judgment is made that the radiation source and the radiation detection section cannot be held in the predetermined positional relationship.

12. A computer-readable medium which stores a program used by a radiological imaging apparatus that causes the radiological imaging apparatus to function as:
   a radiation source that generates radiation irradiating a subject;
   a radiation detection section that detects radiation from the radiation source that passes through the subject;
   a signal detection section that detects signals from a plurality of signal generating sections disposed on the radiation detection section in a manner such that each signal generating section is in a different location;
   a signal comparison section that compares the signals from the plurality of signal generating sections detected by the signal detection section;
   a positional relationship judgment section that makes a judgment as to whether a positional relationship between the radiation detection section and the radiation source is a predetermined positional relationship based on a comparison result from the signal comparison section;
   a position control section that controls a position of at least one of the radiation source and the radiation detection section to maintain the positional relationship between the radiation source and the radiation detection section as the predetermined positional relationship based on a judgment result from the positional relationship judgment section;
   a position control holding section that holds the radiation source and the radiation detection section in the position set by the position control section and fixes the positional relationship between the radiation detection section and the radiation source after the position control section causes the positional relationship to be the predetermined positional relationship;
   a notification section that provides notification in a case where the positional relationship judgment section makes a judgment that the positional relationship is not the predetermined positional relationship while the position control holding section is holding the radiation source and the radiation detection section in the position set by the position control section;
   a position judgment section that makes a judgment as to whether the radiation source and the radiation detection section can be held in the predetermined positional relationship based on a comparison result from the signal comparison section and a range in which the radiation source and the radiation detection section can move; and
   a warning section that warns a user in a case where the position judgment section makes a judgment that the radiation source and the radiation detection section cannot be held in the predetermined positional relationship.

* * * * *